United States Patent
Andersen et al.

(10) Patent No.: US 6,306,631 B1
(45) Date of Patent: Oct. 23, 2001

(54) PPGPP SYNTHETASE AND EXPRESSION SYSTEMS FOR IMPROVED PRODUCTION OF PROTEIN OF INTEREST

(75) Inventors: Jens Tonne Andersen, Naerum (DK); Stanislas Dusko Ehrlich, Paris (FR)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 09/442,055

(22) Filed: Nov. 16, 1999

Related U.S. Application Data

(63) Continuation of application No. PCT/DK98/00261, filed on Jun. 19, 1998.

(30) Foreign Application Priority Data

Jun. 20, 1997 (DK) .......................................... 0726

(51) Int. Cl.[7] ................ C12N 9/00; C12N 9/26; C12N 9/42; C12N 9/10; C12P 21/06
(52) U.S. Cl. .................. 435/183; 435/201; 435/209; 435/208; 435/195; 435/198; 435/193; 435/69.1; 435/233; 435/252.3; 435/252.31; 435/320.1
(58) Field of Search ............... 435/252.5, 252.3, 435/320.1, 201, 209, 208, 195, 198, 193, 252.31, 183, 69.1

(56) References Cited

FOREIGN PATENT DOCUMENTS 222 633  5/1985 (DE) .

OTHER PUBLICATIONS

Swanton et al., BBRC, 46(2), 583–588, Apr. 1992.*
Wendrich et al., Molecular Microbiology, vol. 216, No. 1, pp. 65–79 (1997).
Gropp et al., Gene, vol. 140, pp. 91–96 (1994).
Mechold et al., Journal of Bacteriology, vol. 178, No. 5, pp. 1401–1411 (Mar. 1996).
Metzger et al., Journal of Biological Chemistry, vol. 263, No. 30, pp. 15699–15704 (Oct. 25, 1988).

* cited by examiner

Primary Examiner—Rebecca E. Prouty
Assistant Examiner—M. Monshipouri
(74) Attorney, Agent, or Firm—Elias J. Lambiris, Esq.

(57) ABSTRACT

The present invention relates to a novel ppGpp synthetase and expression systems for improved production of proteins of interest in Gram-positive bacteria, involving use of the novel ppGpp synthetase.

9 Claims, No Drawings

PPGPP SYNTHETASE AND EXPRESSION SYSTEMS FOR IMPROVED PRODUCTION OF PROTEIN OF INTEREST

CROSS-REFERENCES TO RELATED APPLICATIONS

This application is a continuation application of PCT/DK98/00261 filed Jun. 19, 1998 and claims priority under 35 U.S.C. 119 of Danish application no. 0726/97 filed Jun. 20, 1997, the contents of which are fully incorporated herein by reference.

FIELD OF THE INVENTION

This invention relates to a novel ppGpp synthetase and expression systems for improved production of proteins of interest in Gram-positive bacteria, involving use of said novel ppGpp synthetase.

DESCRIPTION OF THE RELATED ART

In gram-positive bacteria secreted proteins are exported across a cell membrane and a cell wall, and are then subsequently released into the external medium.

Gram-positive bacteria such as *B. subtilis, B. amyloliquefaciens, B. licheniformis* have a high capacity for secreting proteins, and indeed, many bacillar extracellular enzymes are used industrially.

A number of proteins are involved in the secretion machinery in gram-positive cells.

WO 94/19471 describes a PrsA protein involved in the secretion machinery of Bacillus, and further describe an expression system for enhancing secretion of exoproteins of interest involving over-expression of the PrsA protein.

Dedhia et al. (Biotechnology and Bioengineering 53:379–386 (1997)) describe gram-negative *E. coli* strains which express smaller than wild-type amounts of ppGpp synthetase (relA). Such gram-negative *E. coli* strains give improved production of a chloramphenicol acetyltransferase (CAT) protein.

SUMMARY OF THE INVENTION

The problem to be solved, by the present invention is to provide an expression system for improved production of a protein of interest in a Gram-positive bacterium, e.g. in a Bacillus strain.

The solution is based on cloned novel DNA sequences from Bacillus species *B. subtilis* (SEQ ID No 1) and *B. amyloliquefaciens* (SEQ ID No 3) which both encode a polypeptide having ppGpp synthetase activity.

The novel DNA sequence information disclosed herein can be used to clone similar DNA sequences from Gram positive bacteria by e.g. standard PCR technology. See e.g. a working example herein (vide infra).

This DNA sequence information provides the possibility of constructing an expression system for improved production of at least one protein of interest in a gram-positive bacterium, wherein said gram-positive bacterium is expressing smaller than wild-type amounts of a polypeptide having ppGpp synthetase activity.

Accordingly, in a first aspect, the present invention provides an isolated polynucleotide molecule selected from the group consisting of (a) polynucleotide molecules encoding a polypeptide having ppGpp synthetase activity and comprising a sequence of nucleotides as shown in SEQ ID NO: 1 from nucleotide 21 to nucleotide 2225; (b) species homologs of (a); (c) polynucleotide molecules that encode a polypeptide having ppGpp synthetase activity that is at least 70% identical to the amino acid sequence of SEQ ID NO: 2 from amino acid residue 1 to amino acid residue 734; (d) molecules complementary to (a), (b) or (c); and (e) degenerate nucleotide sequences of (a), (b), (c) or (d).

Within a second aspect of the invention there is provided an expression vector comprising the following operably linked elements: a transcription promoter; a DNA segment selected from the group consisting of (a) polynucleotide molecules encoding a polypeptide having ppGpp synthetase activity and comprising a sequence of nucleotides as shown in SEQ ID NO: 1 from nucleotide 21 to nucleotide 2225; (b) species homologs of (a); (c) polynuicleotide molecules that encode a polypeptide having ppGpp synthetase activity that is at least 70% identical to the amino acid sequence of SEQ ID NO: 2 from amino acid residue 1 to amino acid residue 734; and (d) degenerate nucleotide sequences of (a), (b), or (c); and a transcription terminator.

Within a third aspect of the present invention there is provided a cultured cell into which has been introduced an expression vector as disclosed above, wherein said cell expresses the polypeptide encoded by the DNA segment.

A fourth aspect of the present invention provides an isolated polypeptide having ppGpp synthetase activity selected from the group consisting of (a) polypeptide molecules comprising a sequence of amino acid residues as shown in SEQ ID NO:2 from amino acid residue 1 to amino acid residue 734; (b) species homologs of (a).

Within another aspect of the present invention there is provided a composition comprising a purified polypeptide according to the invention in combination with other polypeptides.

Within yet another aspect of the present invention there are provided methods for producing a polypeptide according to the invention comprising culturing a cell into which has been introduced an expression vector as disclosed above, whereby said cell expresses a polypeptide encoded by the DNA segment and recovering the polypeptide.

In a further aspect, the present invention relates to an expression system for improved production of at least one protein of interest in gram-positive bacteria, which expression system comprises a gram-positive bacterium expressing smaller than wild-type amounts of a polypeptide according to the invention.

In a final aspect the present invention relates to a method for improved production of at least one protein of interest in a gram-positive bacterium, which method comprises:

i) culturing an expression system according to the invention; and ii) purifying said protein of interest from the resulting culture broth or expression system.

DEFINITIONS

Prior to discussing this invention in further detail, the following terms will first be defined The term "species homolog" is intended to include "ortholog" and/or "paralog".

The term "ortholog" denotes a polypeptide or protein obtained from one species that has homology to an analogous polypeptide or protein from a different species.

The term "paralog" denotes a polypeptide or protein obtained from a given species that has homology to a distinct polypeptide or protein from that same species.

The term "expression vector" denotes a DNA molecule, linear or circular, that comprises a segment encoding a polypeptide of interest operably linked to additional segments that provide for its transcription. Such additional segments may include promoter and terminator sequences, and may optionally include one or more origins of replication, one or more selectable markers, an enhancer, a polyadenylation signal, and the like. Expression vectors are generally derived from plasmid or viral DNA, or may contain elements of both. The expression vector of the invention may be any expression vector that is conveniently subjected to recombinant DNA procedures, and the choice of vector will often depend on the host cell into which the vector it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The term "recombinant expression" or "recombinantly expressed" used herein in connection with expression of a polypeptide or protein is defined according to the standard definition in the art. Recombinant expression of a protein is generally performed by using an expression vector as described immediately above. The term "isolated" when applied to a polynucleotide molecule, denotes that the polynucleotide has been removed from its natural genetic environment and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774–78, 1985). The term "an isolated polynucleotide" may alternatively be termed "a cloned polynucleotide".

When applied to a protein, the term "isolated" indicates that the protein is found in a condition other than its native environment. In a preferred form, the isolated protein is substantially free of other proteins, particularly other homologous proteins (i.e. "homologous impurities" (see below)). It is preferred to provide the protein in a highly purified form, i.e., greater than 80% pure, more preferably greater than 95% pure, and even more preferably greater than 99% pure, as determined by SDS-PAGE.

The term "homologous impurities" means any impurity (e.g. another polypeptide than the polypeptide of the invention) which originate from the homologous cell where the polypeptide of the invention is originally obtained from.

The term "obtained from" as used herein in connection with a specific microbial source, means that the polynucleotide and/or polypeptide produced by the specific source, or by a cell in which a gene from the source have been inserted.

The term "operably linked" when referring to DNA segments, denotes that the segments are arranged so that they function in concert for their intended purposes, e.g. transcription initiates in the promoter and proceeds through the coding segment to the terminator.

The term "polynucleotide" denotes a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules.

The term "complements of polynucleotide molecules" denotes polynucleotide molecules having a complementary base sequence and reverse orientation as compared to a reference sequence. For example, the sequence 5' ATG-CACGGG 3' is complementary to 5' CCCGTGCAT 3'.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "promoter" denotes a portion of a gene containing DNA sequences that provide for the binding of RNA polymerase and initiation of transcription. Promoter sequences are commonly, but not always, found in the 5' non-coding regions of genes.

The term "secretory signal sequence" denotes a DNA sequence that encodes a polypeptide (a "secretory peptide" that, as a component of a larger polypeptide, directs the larger polypeptide through a secretory pathway of a cell in which it is synthesized. The larger peptide is commonly cleaved to remove the secretory peptide during transit through the secretory pathway.

The term "expression system" for improved production of a protein of interest in gram-positive bacteria, denotes a gram-positive bacterium which express smaller than wild-type amounts of a polypeptide having ppGpp synthetase activity according to the invention. The protein of interest may e.g. be a recombinantly expressed protein.

The term "wildtype amounts" used herein in connection with an expression system as described immediately above, denotes the wild-type (native) amounts of expression level of the polypeptide according to the invention, i.e. the amount of expression level before the gram-positive strain has been modified to express smaller amounts of said polypeptide.

The term "exoprotein" denotes a protein which is secreted from a cell of interest. An exoprotein generally comprise a secretory signal sequence as described above.

The term "ppGpp synthetase" denotes a ppGpp synthetase enzyme defined according to the art.

Synthesis of ppGpp is in *E. coli* governed by at least two ways (Dedhia et al. (Biotechnology and Bioengineering 53:379–386 (1997)). The enzyme ppGpp synthetase I (PSI) (EC 2.7.6.5) encoded by the relA gene in *E. coli* is responsible for ppGpp synthesis during the stringent response to amino acid deprivation (Block, R., Haseltine, W. A. 1974. In vitro synthesis of ppGpp and ppGppp, pp. 747–761. In: M. Nomura, A. Tissieres, and P. Lengyel (eds.), Ribosomes. Cold Spring Harbor Press, Cold Spring Harbor N.Y.). When growth of the bacterium is slowed by the depletion of a primary carbon source, the stringent response is activated by a pathway that is independent of the relA gene (Hernandez, V. J., Bremer, H. 1991. *E. coli* ppGpp synthetase II activity requires spoT. J. Biol. Chem. 266:5991–5999). A second enzyme, ppGpp synthetase II (PSII), encoded by the spoT gene, is responsible for catalyzing ppGpp synthesis (Hernandez, V. J., Bremer, H. 1991. *E. coli* ppGpp synthetase II activity requires spoT. J. Biol. Chem. 266:5991–5999).

In the present context "ppGpp synthetase" is intended to cover both an enzyme having ppGpp synthetase I activity (EC 2.7.6.5) and/or an enzyme having ppGpp synthetase II activity as described above.

Alternatively the term "ppGpp synthetase" may be termed "(p)ppGpp synthetase".

The term "ppGpp synthetase gene" is intended to cover a DNA sequence encoding a polypeptide with ppGpp synthetase activity.

DETAILED DESCRIPTION OF THE INVENTION
HOW TO USE A SEQUENCE OF THE INVENTION TO GET OTHER RELATED SEQUENCES:

The disclosed sequence information herein relating to a polynucleotide sequence encoding a ppGpp synthetase of the invention can be used as a tool to identify other homologous ppGpp synthetases. For instance, polymerase chain reaction (PCR) can be used to amplify sequences encoding other homologous ppGpp synthetases from a variety of microbial sources, in particular of different Bacillus species.

For further details reference is made to a working example herein (vide infra).

ASSAY FOR ACTIVITY TEST

A polypeptide of the invention having ppGpp synthetase activity may be tested for ppGpp synthetase activity according to standard test procedures known in the art, such as by using UV absorbance at 254 nm after nucleotide separation by ion-pair reversed phase high-performance liquid chromatography. For further details reference is made to Baracchini et al (Mol Gen Genet (1988) 213:379–387).

A protein of interest produced by use of an expression system of the invention may be tested for activity by standard activity assays relating to said protein of interest. In particular when the protein of interest is an enzyme a number of relevant enzyme activity assays are described in the art. For a person skilled in the art it is routine work, in particular for enzymes, to identify a useful assay relating to the protein of interest.

POLYNUCLEOTIDES:

Within preferred embodiments of the invention an isolated polynucleotide of the invention will hybridize to similar sized regions of SEQ ID NO:1, or a sequence complementary thereto, under at least medium stringency conditions.

In particular polynucleotides of the invention will hybridize to a double-stranded DNA probe comprising the sequence shown in positions 21–2225 in SEQ ID NO:1, under at least medium stringency conditions, but preferably at high stringency conditions as described in detail below.

Suitable experimental conditions for determining hybridization at medium or high stringency between a nucleotide probe and a homologous DNA or RNA sequence involves presoaking of the filter containing the DNA fragments or RNA to hybridize in 5×SSC (Sodium chloride/Sodium citrate, Sambrook et al. 1989) for 10 min, and prehybridization of the filter in a solution of 5×SSC, 5×Denhardt's solution (Sambrook et al. 1989), 0.5% SDS and 100 µg/ml of denatured sonicated salmon sperm DNA (Sambrook et al. 1989), followed by hybridization in the same solution containing a concentration of 10 ng/ml of a random-primed (Feinberg, A. P. and Vogelstein, B. (1983) *Anal. Biochem.* 132:6–3), $^{32}$P-dCTP-labeled (specific activity >1×10$^9$ cpm/µg) probe for 12 hours at ca. 45° C. The filter is then washed twice for 30 minutes in 2×SSC, 0.5% SDS at least 60° C. (medium stringency), still more preferably at least 65° C. (medium/high stringency), even more preferably at least 70° C. (high stringency), and even more preferably at least 75° C. (very high stringency).

Molecules to which the oligonucleotide probe hybridizes under these conditions are detected using an x-ray film.

As previously noted, the isolated polynucleotides of the present invention include DNA and RNA. Methods for isolating DNA and RNA are well known in the art.

Total RNA can be prepared using guanidine HCl extraction followed by isolation by centrifugation in a CsCl gradient (Chirgwin et al., *Biochemistry* 18:52–94, 1979). Poly (A)$^+$ RNA is prepared from total RNA using the method of Aviv and Leder (*Proc. Natl. Acad. Sci. USA* 69:1408–1412, 1972). Complementary DNA (cDNA) is prepared from poly (A)+ RNA using known methods.

Polynucleotides encoding polypeptides having ppGpp synthetase activity of the invention are then identified and isolated by, for example, hybridization or PCR.

The present invention further provides counterpart polypeptides and polynucleotides from different bacterial strains (orthologs or paralogs). Of particular interest are ppGpp synthetase polypeptides from gram-positive strains, including species of Bacillus such as *Bacillus subtilis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus thuringiensis, Bacillus clausii*, or in particular *Bacillus licheniformis*.

The polynucleotide of the invention shown in SEQ ID No 1 is obtained from the *Bacillus subtilis* strain 168 (NCIB 10106). The polynucleotide of SEQ ID NO:1 encodes a polypeptide exhibiting ppGpp snthetase activity of SEQ ID NO:2. The polypeptide of SEQ ID NO:2 is designated herein relA-Bac.

Species homologs of a polypeptides having ppGpp synthetase activity of the invention can be cloned using information and compositions provided by the present invention in combination with conventional cloning techniques. For example, a cDNA can be cloned using mRNA obtained from cell type that expresses the protein. Suitable sources of mRNA can be identified by probing Northern blots with probes designed from the sequences disclosed herein. A library is then prepared from mRNA of a positive cell. A cDNA encoding an polypeptide having ppGpp synthetase activity of the invention can then be isolated by a variety of methods, such as by probing with a complete or partial cDNA or with one or more sets of degenerate probes based on the disclosed sequences. A cDNA can also be cloned using the polymerase chain reaction, or PCR (Mullis, U.S. Pat. No. 4,683,202), using primers designed from the sequences disclosed herein. Within an additional method, the cDNA library can be used to transform or transfect host cells, and expression of the cDNA of interest can be detected with an antibody to relA-bac or by an activity test relating to a polypeptide having ppGpp synthetase activity. Similar techniques can also be applied to the isolation of genomic clones.

POLYPEPTIDES:

The present invention also provides isolated ppGpp synthetase polypeptides that are substantially homologous to the polypeptides of SEQ ID NO:2 and their species homologs (paralogs or orthologs). The term "substantially homologous" is used herein to denote polypeptides having 70%, more preferably at least 80%, sequence identity to the sequences shown in SEQ ID NO:2 or their orthologs or paralogs. Such polypeptides will more preferably be at least 90% identical, and most preferably 95% or more identical to SEQ ID NO:2 or its orthologs or paralogs. Percent sequence identity is determined by conventional methods, by means of computer programs known in the art such as GAP provided in the GCG program package (Program Manual for the Wisconsin Package, Version 8, August 1994, Genetics Computer Group, 575 Science Drive, Madison, Wis. USA 53711) (Needleman, S. B. and Wunsch, C. D., (1970), Journal of Molecular Biology, 48, 443–453). GAP is used with the following settings for polypeptide sequence comparison: GAP creation penalty of 3.0 and GAP extension penalty of 0.1.

Sequence identity of polynucleotide molecules is determined by similar methods using GAP with the following settings for DNA sequence comparison: GAP creation penalty of 5.0 and GAP extension penalty of 0.3.

Substantially homologous proteins and polypeptides are characterized as having one or more amino acid substitutions, deletions or additions. These changes are preferably of a minor nature, that is conservative amino acid substitutions (see Table 2) and other substitutions that do not significantly affect the folding or activity of the protein or polypeptide; small deletions, typically of one to about 30 amino acids; and small amino- or carboxyl-terminal extensions, such as an amino-terminal methionine residue, a small linker peptide of up to about 20–25 residues, or a small extension that facilitates purification (an affinity tag), such as a poly-histidine tract, protein A (Nilsson et al., *EMBO J.* 4:1075, 1985; Nilsson et al., *Methods Enzymol.* 198:3, 1991. See, in general Ford et al., *Protein Expression and Purification* 2: 95–107, 1991, which is incorporated herein by reference. DNAs encoding affinity tags are available from commercial suppliers (e.g., Pharmacia Biotech, Piscataway, N.J.; New England Biolabs, Beverly, Mass.).

TABLE I

Conservative amino acid substitutions

| | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

In addition to the 20 standard amino acids, non-standard amino acids (such as 4-hydroxyproline, 6-N-methyl lysine, 2-aminoisobutyric acid, isovaline and a-methyl serine) may be substituted for amino acid residues of a polypeptide according to the invention. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, or preferably, are commercially available, and include pipecolic acid, thiazolidine carboxylic acid, dehydroproline, 3- and 4-methylproline, and 3,3-dimethylproline.

Essential amino acids in the ppGpp synthetase polypeptides of the present invention can be identified according to procedures known in the art, such as site-directed mutagenesis or alanine-scanning mutagenesis (Cunningham and Wells, *Science* 244: 1081–1085, 1989). In the latter technique, single alanine mutations are introduced at every residue in the molecule, and the resultant mutant molecules are tested for biological activity (i.e., ppGpp synthetase activity) to identify amino acid residues that are critical to the activity of the molecule. See also, Hilton et al., *J. Biol. Chem.* 271:4699–4708, 1996. Sites of ligand-receptor or other biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306–312, 1992; Smith et al., *J. Mol. Biol.* 224:899–904, 1992; Wlodaver et al., *FEBS Lett.* 309:59–64, 1992. The identities of essential amino acids can also be inferred from analysis of homologies with polypeptides which are related to a polypeptide according to the invention.

Multiple amino acid substitutions can be made and tested using known methods of mutagenesis, recombination and/or shuffling followed by a relevant screening procedure, such as those disclosed by Reidhaar-Olson and Sauer (*Science* 241:53–57, 1988), Bowie and Sauer (*Proc. Natl. Acad. Sci. USA* 86:2152–2156, 1989), WO95/17413, or WO 95/22625. Briefly, these authors disclose methods for simultaneously randomizing two or more positions in a polypeptide, or recombination/shuffling of different mutations (WO95/17413, WO95/22625), followed by selecting for functional a polypeptide, and then sequencing the mutagenized polypeptides to determine the spectrum of allowable substitutions at each position. Other methods that can be used include phage display (e.g., Lowman et al., *Biochem.* 30:10832–10837, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

Mutagenesis/shuffling methods as disclosed above can be combined with high-throughput, automated screening methods to detect activity of cloned, mutagenized polypeptides in host cells. Mutagenized DNA molecules that encode active polypeptides can be recovered from the host cells and rapidly sequenced using modern equipment. These methods allow the rapid determination of the importance of individual amino acid residues in a polypeptide of interest, and can be applied to polypeptides of unknown structure.

Using the methods discussed above, one of ordinary skill in the art can identify and/or prepare a variety of polypeptides that are substantially homologous to residues 1 to 734 of SEQ ID NO: 2 and retain the ppGpp synthetase activity of the wild-type protein.

PROTEIN PRODUCTION:

The polypeptides of the present invention, including full length proteins, fragments thereof and fusion proteins, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Bacterial cells, particularly cultured cells of gram-positive organisms, are preferred. Gram-positive cells from the genus of Bacillus are especially preferred, such as *Bacillus subtilis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus thuringiensis, Bacillus clausii,* or in particular *Bacillus licheniformis.*

Techniques for manipulating cloned DNA molecules and introducing exogenous DNA into a variety of host cells are disclosed by Sambrook et al., *Molecular Cloning: A Laboratory Manual*, 2nd ed., Cold Spring Harbor Laboratory Press, Cold Spring Harbor, N.Y., 1989; Ausubel et al. (eds.), *Current Protocols in Molecular Biology*, John Wiley and Sons, Inc., NY, 1987; and (*Bacillus subtilis* and Other Gram-Positive Bacteria, Sonensheim et al., 1993, American Society for Microbiology, Washington D.C.), which are incorporated herein by reference.

In general, a DNA sequence encoding a ppGpp synthetase polypeptide of the present invention is operably linked to other genetic elements required for its expression, generally including a transcription promoter and terminator within an expression vector. The vector will also commonly contain one or more seco lectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a polypeptide into the secretory pathway of a host cell, a secretory signal sequence (also known as a leader sequence, prepro sequence or pre sequence) is provided in the expression vector. The secretory signal sequence may be that of the polypeptide, or may be derived from another secreted protein or synthesized de novo. The secretory signal sequence is joined to the DNA sequence in the correct reading frame. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830).

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

PROTEIN ISOLATION:

Expressed recombinant polypeptides (or chimeric polypeptides) can be purified using fractionation and/or conventional purification methods and media. Ammonium sulfate precipitation and acid or chaotrope extraction may be used for fractionation of samples. Exemplary purification steps may include hydroxyapatite, size exclusion, FPLC and reverse-phase high performance liquid chromatography. Suitable anion exchange media include derivatized dextrans, agarose, cellulose, polyacrylamide, specialty silicas, and the like. PEI, DEAE, QAE and Q derivatives are preferred, with DEAE Fast-Flow Sepharose (Pharmacia, Piscataway, N.J.) being particularly preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers.

Selection of a particular method is a matter of routine design and is determined in part by the properties of the chosen support. See, for example, *Affinity Chromatography: Principles & Methods*, Pharmacia LKB Biotechnology, Uppsala, Sweden, 1988.

It is preferred to purify the protein to >80% purity, more preferably to >90% purity, even more preferably >95%, and particularly preferred is a nearly complete pure state, that is greater than 99.9% pure with respect to contaminating macromolecules, particularly other proteins and nucleic acids, and free of infectious and pyrogenic agents. Preferably, a purified protein is substantially free of other proteins, particularly other proteins of bacterial origin, and especially of gram-positive bacterial origin. The degree of purity is determined by SDS-PAGE.

Polypeptides of the invention or fragments thereof may also be prepared through chemical synthesis. Polypeptides of the invention may be monomers or multimers; glycosylated or non-glycosylated; pegylated or non-pegylated; and may or may not include an initial methionine amino acid residue.

USES OF POLYNUCLEOTIDE/POLYPEPTIDE:

The information disclosed herein relating to a polypeptide having ppGpp synthetase activity of the invention is essential to construct an expression system for improved production of a protein of interest in gram-positive bacteria as described in further details below.

EXPRESSING SYSTEM FOR ENHANCING SECRETION OF EXOPROTEINS IN GRAM-POSITIVE BACTERIA:

An aspect of the present invention relates to an expression system for improved production of at least one protein of interest in gram-positive bacteria, which expression system comprises a gram-positive bacterium expressing smaller than wild-type amounts of a polypeptide according to the invention.

Preferably the protein of interest in an exoprotein.

Preferably, the term "expression system for improved production of at least one protein of interest" is an expression system having one or more of the improved properties described immediately below.

Improved properties for an expression system of the invention include properties such as an improved ability to utilize growth media, an ability to grow to higher cell densities, an ability to grow in minimal medium, sporulation deficiency of the production hosts, increased expression of the protein of interest, measured either in terms of the amount of the protein of interest accumulated in the fermentation broth or as the production of the protein of interest per cell mass per time unit, reduced tendency of the fermentation broths to form foam, reduced viscosity of the fermentation broth, reduced degradation of the protein product produced by the production host, reduced tendency of the producer organism to lyse (reduced autolysis), a higher fraction of highly producing cells in the producing culture, a reduced formation of pigments or colored compounds during fermentation, and improved fermentation broths allowing more easy and efficient recovery steps and thus result in improved recovery yields.

As described above a relA-Bac polypeptide of the invention is a polypeptide which is having ppGpp synthetase activity.

Advantages of having smaller than wildtype amounts of ppGpp in the production organism:

ppGpp is a true alarmone, i.e., its concentration is very low under normal growth conditions (P. Neubauer et al (J. of Biotechnology (1995) 43:195–204)) and the intracellular concentration of ppGpp increases rapidly when the organism is exposed to starvation or other stress factors. When the intra cellular ppGpp concentration is increasing the ribosomal RNA (rRNA) concentration is decreasing which again may result in:

Decrease in translation and thereby a decrease in the desired protein production.

Higher instability of a given mRNA because the number of ribosomes loaded on the mRNA is reduced resulting in a less protected mRNA that could lead to a higher nuclease activity.

Reduced elongation rate of messenger RNA chains (U. Vogel et al. (J. of Biological Chemistry (1997) 272:12265–12271)).

Accordingly, in order to obtain an expression system for improved production of a protein of interest, it is advantageously to express smaller than wildtype amount of a ppGpp synthetase in the production cell used to express said protein of interest.

A number of techniques to be able to express smaller amounts of a polypeptide of interest in gram-positive bacteria are known in the art, in particular for a preferred gram-positive bacterium of the genus of Bacillus (*Bacillus subtilis* and other Gram-Positive Bacteria, Sonensheim et al., 1993, American Society for Microbiology, Washington D.C.).

Suitable techniques to express smaller amounts of a polypeptide having ppGpp synthetase activity of the invention include techniques such as deletion or otherwise destruction (e.g. by destroying the correct reading frame) of a ppGpp synthetase gene (some or all copies thereof) of the invention (e.g. on the chromosome of the gram-positive bacterium), truncation of a ppGpp synthetase gene (e.g. by introduction of STOP-codons), using anti-sense mRNA against the transcribed mRNA from a ppGpp synthetase gene, and/or altering the regulatory elements to increase expression, e.g. use of weak promoters, and so forth. For further details reference is made to (Sambrook et al. (1989) Molecular cloning: A laboratory manual, Cold Spring Harbor lab., Cold Spring Harbor, N.Y.; Ausubel, F. M. et al. (eds.) "Current protocols in Molecular Biology". John Wiley and Sons, 1995; Harwood, C. R., and Cutting, S. M. (eds.) "Molecular Biological Methods for Bacillus". John Wiley and Sons, 1990).

Based on the DNA and/or amino acid sequence information provided herein, selection of a particular strategy to express smaller than wild-type amounts of a polypeptide having ppGpp synthetase activity of the invention in a gram-positive bacterium is a matter of routine for a person skilled in the art.

To determine the degree of decreased expression of a polypeptide having ppGpp synthetase activity of the invention any relevant ppGpp synthetase activity assay/test may be used (suitable assays are described herein (vide supra)). The amount of a polypeptide of the invention having ppGpp synthetase activity produced before and after modification of the gram-positive cell is measured, and the degree of decreased expression may be measured relative to the unmodified wild-type (control) cell.

The degree of decreased expression of a polypeptide having ppGpp synthetase activity according to the invention is preferably a two fold decreased expression, more preferably a four fold decreased expression, and even more preferably a ten fold decreased expression, and most preferably the expression of a polypeptide, according to the invention, having ppGpp synthetase activity is completely disrupted.

Preferably a polypeptide having ppGpp synthetase activity of the invention is a polypeptide obtained from a species of Bacillus, such as *Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus thuringiensis, Bacillus licheniformis, Bacillus clausii*, or in particular from *Bacillus subtilis*.

The gram-positive bacteria in the expression system of the invention may be cultured by conventional methods as described for host cells in the section "PROTEIN PRODUCTION" (vide supra).

Preferably the gram-positive bacterium is a species of Bacillus such as *Bacillus subtilis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus thuringiensis, Bacillus clausii*, or *Bacillus licheniformis*.

Relatively to the gram-positive bacterium, the protein of interest may be both a homologous protein, or a heterologous protein.

Preferably, the protein of interest is recombinantly expressed.

The protein of interest may be any protein of interest. However preferably the protein of interest is an exoprotein, and in particular a protease, a lipase, an amylase, a galactosidase, a pullanase, a cellulose, a glucose isomerase, a protein disulphide isomerase, a CGT ase (cyclodextrin gluconotransferase), a phytase, a glucose oxidase, a glucosyl transferase, a laccase, a xylanase, a bacterial protein toxin, a microbial surface protein, a viral protein, or a pharmaceutical protein.

To determine the degree of improved production of a protein of interest, preferably an exoprotein of interest, any relevant activity assay/test, corresponding to the protein (e.g. exoprotein) of interest, may be used.

The degree of improved production of a protein of interest may be determined relative to the production level of the protein in the gram-positive strain before the strain has been modified to express smaller amounts of a polypeptide according to the invention.

Use of the expression system of the invention results in at least 2 fold improved production of at least one protein of interest, more preferably at least 4 fold improved production of at least one protein of interest, and even more preferably at least 10 fold improved production of at least one protein of interest.

The protein of interest may be isolated by standard procedures as e.g. described in the section "PROTEIN ISOLATION" (vide supra).

Further the present invention relates to a method for improved production of at least one protein of interest in a gram-positive bacterium, which method comprises:
 i) culturing an expression system according to the invention; and
 ii) purifying said protein of interest from the resulting culture broth or expression system.

In a preferred embodiment said culturing is done as a fed-batch fermentation.

A fed-batch fermentation is a standard fermentation procedure especially for large scale industrial production of a protein of interest.

Fed-batch fermentation is generally described in BASIC Biochemical Engineering (Bungay, Henry R. BASIC Biochemical Engineering (2nd ed.).Troy: BiLine Associates, 1993.) as the type of system where "nutrient is added when its concentration falls below some set point." Usually the addition of the nutrient is controlled by a computer for precision. A preferred way to control the addition of the feed is to monitor the concentration of the nutrient itself in the fermenter or reactor vessel.

The nutrient is added in several doses, to ensure that there is not too much of the nutrient present in the fermenter at any time. If too much of a nutrient is present, it may inhibit the growth of the cells. By adding the nutrient in a controlled manner, the reaction can proceed at a high rate of production without getting overloaded.

An example of a suitable fed-batch fermentation is described by Neubauer, P. et al. (1995. Journal of Biotechnology 43 p.197–198).

The theory behind this preferred embodiment is that the cellular content of many direct participants in protein synthesis such as RNA polymerase, elongation factors and initiation factors are decreased as a result of nutrient and energy starvation and mediated by the (p)ppGpp synthetase encoded by the relA gene Dedhia, N. et. al. (1997) Biotechnology and Bioengineering 53 (4) p 379–386.

Thereby, by using a gram-positive bacteria with decreased expression of a polypeptide having ppGpp synthetase activity according to the invention, the production of a protein of interest will improve in such a fed-batch fermentation.

Alternatively, said culturing may e.g. be done by using one of below mentioned standard fermentation techniques:

Batch fermentation: In a batch fermentation the cells will grow, after inoculation, until one of the substrate components is exhausted or an inhibitor is accumulated; or Continuous Cultivation, by of one following standard techniques;
 chemostat nutrient is fed at constant rate;
 turbidostat employing feedback control of pumping rate to maintain a fixed turbidity of the culture. The controller of a turbidostat slows feeding when the cell concentration is below the set point so that growth can restore the turbidity. If the set point is exceeded, the pump speeds up to dilute the cell concentration; or
 nustat, nutritstat, or auxostat (names are synonymous) feeding medium to hold a factor constant.

The invention is further illustrated by the following non-limiting examples.

MATERIALS AND METHODS

General Molecular Biology Methods:

Unless otherwise mentioned the DNA manipulations and transformations were performed using standard methods of molecular biology (Sambrook et al. (1989) Molecular cloning: A laboratory manual, Cold Spring Harbor lab., Cold Spring Harbor, N.Y.; Ausubel, F. M. et al. (eds.) "Current protocols in Molecular Biology". John Wiley and Sons, 1995; Harwood, C. R., and Cutting, S. M. (eds.) "Molecular Biological Methods for Bacillus". John Wiley and Sons, 1990).

Enzymes for DNA manipulations were used according to the specifications of the suppliers.

Enzymes for DNA Manipulations

Unless otherwise mentioned all enzymes for DNA manipulations, such as e.g. restiction endonucleases, ligases etc., are obtained from New England Biolabs, Inc.

EXAMPLES

Example 1

Identification of Others ppGpp Synthethases Obtained from Different Bacillus.

PCR Reactions.

On Colonies:

A reisolated colony which had been incubated 18 hours on LB agar plates containing 10 $\mu$g/ml kanamycin, 10 mM pottasium phosphate pH 7,0 and 0,4% glucose was suspended in 10 $\mu$l 1×PCR buffer (Super Taq™ DNA polymerase) heated to 96° C. for 5 minutes, spun 20,000×g for 2 minutes. From the supernatant, 5 $\mu$l was used as template in a PCR reaction (30 cycles) using the different primers below and the Super Taq™ DNA polymerase following the manufactures' instructions (Enzyme technologies Ltd.).

Primers for PCR reactions. DNA primers (primer:#104775 to #104780) with a oligo nucleotide composition with identity to the B. subtilis relA-Bac sequence shown in SEQ ID No 1 (underlined) has been used for amplifying DNA fragments from B. subtilis, B. amyloliquefaciens, B. lentus and B. licheniformis.

Positions relates to the DNA sequence shown in SEQ ID No 1.

Non-underline primer sequence are linker sequence for cloning purpose, which comprise a suitable site for restriction enzyme digestion.

Primers for the 5'-end of the relA-Bac gene from B. subtilis: (sense primers)
 #104775: 5'-CCG AAT TC A AAG GTG ATT CCA TGG CGA ACG-3' (Pos: 9 to 30)(SEQ ID No: 5)

104776: 5'-CCG AAT TC G GTG ATT CCA TGG CGA ACG-3' (Pos: 12 to 30) (SEQ ID NO: 6)

Primers for the 3'-end of internal parts of the relA-Bac gene of *B. subtilis*. (anti-sense primers)

104777: 5'-GCG GAT CCG CTT TAG GCC C-3' (Pos: 987 to 969) (SEQ ID NO: 7)

104778: 5'-CAT GCA TTT CAA AGG TGC GG-3' (Pos: 1020 to 1001)(SEQ ID NO: 8)

Primers for the 3'-end of the relA-Bac gene of *B. subtilis*. (anti-sense primers)

104779: 5'-CCT TTA GTT CAT GAC GCG GCG C-3' (Pos: 2228 to 2207)(SEQ ID NO: 9)

104780: 5'-GTG TTT AGC GGC CGC TGA ACAACT AAT CTC-3' (Pos: 2277 to 2256) (SEQ ID NO: 10)

113554: 5'-ATA AGC ATG CGC TGA ACA ACT AAT CTC-3' (Pos: 2256 to 2239)(SEQ ID NO: 11)

Analyses of PCR Products.

PCR products from *B. subtilis, B. amyloliquefaciens, B. licheniformis,* and *B. lentus* were analyzed on a 0.7% agarose gel containing Ethidium bromide to determine if DNA was present and if present an estimate of the size of the DNA.

The expected size PCR product were obtained.

*B. amyloliquefaciens*: PCR fragment size approximately 980 bp, with primers 104775, 104777.

*B. lentus*: PCR fragment size approximately 980 bp and 680, with primers 104775, 104777. Both PCR fragment may be used further to clone a *B. lentus* ppGpp synthetase.

*B. licheniformis*: PCR fragment size approximately 800 bp, with primers 104776, 104778; and PCR fragment size approximately 1900 bp, with primers 104776, 104779.

The PCR amplified DNA fragments are sequenced and this sequence information is used to clone *B. amyloliquefaciens, B. licheniformis,* and *B. lentus* ppGpp synthethases according to the invention. The cloning is performed according to standard procedure in the art.

Cloning of *B. Amnyloliquefaciens* Full Length ppGpp Syn-thethases:

Using the B.amyloliquefaciens PCR fragment sized approximately 980 bp amplified with primers 104775, 104777 (see above) together with PCR (anti-sense) primer #113554.

A PCR fragment from a *B. amyloliquefaciens* strain was obtained and DNA sequenced on an automatic DNA sequencer according to the manufactures protocol.

This DNA sequence and corresponding mature protein sequence are shown in SEQ ID No. 3 and 4. The polypeptide has been designated relA-BacII and is obtained from a *Bacillus amyloliquefaciens* strain.

Example 2

Homology/Basis for Prediction:

The present invention is based in part upon the discovery of a novel polynucleotide sequence obtained form a *Bacillus subtilis* strain that encodes a polypeptide having ppGpp synthetase activity and having homology to other microbial ppGpp syntheases. The polypeptide has been designated relA-Bac.

The criteria for defining novel polypeptides having ppGpp synthetase activity of the present invention were initially identified by querying to the public known database Genebank (EMBL, Heidelberg) for homologous sequences to the novel relA-Bac sequence of the invention.

Using a conventional percent sequence identity program as described in further details herein (vide infra) the DNA sequence identity of relA-Bac (SEQ ID NO: 1) to prior art known ppGpp syntheases are shown in table I below, and the corresponding amino acid sequence identity are shown in Table II.

TABLE II

Homology between DNA sequences.

The sequences used for similarity is the coding DNA sequences (CDS) from the GeneBank entries at EMBLwith the locus listed in the scheme.
GB_BA:SEDEXB ! X72832 *S. equisimilis*
GB_BA:VSU13769 ! U13769 Vibrio sp.
GB_BA:ECOSPOT ! M24503 *E. coli*
GB_BA:ECORELA ! J04039 *E. coli*

| GB_BA: | bsrela.orf | ecorela.orf | ecospot. orf | sedexb.orf | vsu13769. orf |
|---|---|---|---|---|---|
| relA-Bac | 100 | 50 | 51 | 59 | 50 |
| ecorela.orf | 50 | 100 | 48 | 49 | 62 |
| ecospot.orf | 51 | 48 | 100 | 51 | 45 |
| sedexb.orf | 59 | 49 | 51 | 100 | 49 |
| vsu13769.orf | 50 | 62 | 45 | 49 | 100 |

Homology between peptide sequences encoded by the above DNA sequences.

| | bsrela.pep | ecorela.pep | ecospot.pep | sedexb.pep | vsu13769.pep |
|---|---|---|---|---|---|
| relA-Bac | 100 | 38 | 41 | 53 | 37 |
| ecorela.pep | 38 | 100 | 32 | 36 | 65 |
| ecospot.pep | 41 | 32 | 100 | 42 | 32 |
| sedexb.pep | 53 | 36 | 42 | 100 | 34 |
| vsu13769.pep | 37 | 65 | 32 | 34 | 100 |

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for producing a protein of interest, which comprises:
   (a) culturing a gram-positive bacterial strain, wherein (i) a DNA sequence encoding the protein of interest has been introduced into the strain, (ii) the strain produces less of a polypeptide having ppGpp synthetase activity than the corresponding wild-type strain, and (iii) the polypeptide having ppGpp synthetase activity has an amino acid sequence that is at least 70% identical to the amino acid sequence of amino acid residues 1 to 734 of SEQ ID NO:2; and
   (b) purifying the protein of interest from the resulting culture broth or expression system.

2. The method of claim 1, wherein the gram-positive bacterial strain is a Bacillus strain.

3. The method of claim 2, wherein the gram-positive bacterial strain is a *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus stearothermophilus, Bacillus subtilis*, or *Bacillus thuringiensis* strain.

4. The method of claim 1, wherein the protein of interest is a homologous protein.

5. The method of claim 1, wherein the protein of interest is a heterologous protein.

6. The method of claim 5, wherein the protein is an exoprotein.

7. The method of claim 1, wherein the protein of interest is an amylase, bacterial protein toxin, cellulase, cyclodextrin gluconotransferase, galactosidase, glucose isomerase, glucose oxidase, glucosyl transferase, laccase, lipase, microbial surface protein, pharmaceutical, phytase, protease, protein disulphide isomerase, pullanase, xylanase, or viral protein.

8. The method of claim 1, wherein the culturing is performed as a fed-batch fermentation.

9. The method of claim 1, wherein the polypeptide having ppGpp synthetase activity has an amino acid sequence which comprises amino acid residues 1 to 734 of SEQ ID NO: 2.

* * * * *

SEQUENCE LISTING

<160> NUMBER OF SEQ ID NOS: 11

<210> SEQ ID NO 1
<211> LENGTH: 2278
<212> TYPE: DNA
<213> ORGANISM: relA-bac
<220> FEATURE:
<221> NAME/KEY: CDS
<222> LOCATION: (21)...(2222)

<400> SEQUENCE: 1

```
attttaaaaa aggtgattcc atg gcg aac gaa caa gta ttg act gcc gag caa      53
                     Met Ala Asn Glu Gln Val Leu Thr Ala Glu Gln
                      1               5                  10 gtt ata gat aaa gca cgc agc tat cta tct gat gag cat atc gca ttt       101
Val Ile Asp Lys Ala Arg Ser Tyr Leu Ser Asp Glu His Ile Ala Phe
             15                  20                  25 gtc gaa aaa gca tat ctg tac gct gaa gat gct cat cgc gag caa tac       149
Val Glu Lys Ala Tyr Leu Tyr Ala Glu Asp Ala His Arg Glu Gln Tyr
         30                  35                  40 cgc aaa tcg ggc gag cca tat att att cat ccg att cag gtt gcg ggg       197
Arg Lys Ser Gly Glu Pro Tyr Ile Ile His Pro Ile Gln Val Ala Gly
     45                  50                  55 ata ctc gtt gat ctt gaa atg gac cct tcc aca atc gcg ggc gga ttt       245
Ile Leu Val Asp Leu Glu Met Asp Pro Ser Thr Ile Ala Gly Gly Phe
 60                  65                  70                  75 ttg cac gat gtc gtg gaa gat aca gat gtg acg ctc gat gac ctg aaa       293
Leu His Asp Val Val Glu Asp Thr Asp Val Thr Leu Asp Asp Leu Lys
                 80                  85                  90 gaa gca ttt tcc gaa gaa gtg gca atg ctt gta gac ggc gta acg aaa       341
Glu Ala Phe Ser Glu Glu Val Ala Met Leu Val Asp Gly Val Thr Lys
             95                 100                 105 ctc ggc aaa att aaa tat aaa tct caa gag gaa cag cag gcg gaa aat       389
Leu Gly Lys Ile Lys Tyr Lys Ser Gln Glu Glu Gln Gln Ala Glu Asn
        110                 115                 120 cat cgc aaa atg ttt gtc gct atg gct caa gat atc agg gtc ata ttg       437
His Arg Lys Met Phe Val Ala Met Ala Gln Asp Ile Arg Val Ile Leu
    125                 130                 135 atc aag ctg gcg gat cgt ctt cac aat atg cgg aca ctg aaa cat ctg       485
Ile Lys Leu Ala Asp Arg Leu His Asn Met Arg Thr Leu Lys His Leu
140                 145                 150                 155 cct cag gaa aaa cag cgg aga atc tcc aat gaa acg ctg gaa att ttt       533
Pro Gln Glu Lys Gln Arg Arg Ile Ser Asn Glu Thr Leu Glu Ile Phe
                160                 165                 170 gct cct ttg gcg cat cgt ctc ggg att tca aaa att aag tgg gaa ttg       581
Ala Pro Leu Ala His Arg Leu Gly Ile Ser Lys Ile Lys Trp Glu Leu
            175                 180                 185 gaa gat acg gcg ctc cgt tat ttg aac cct cag caa tat tac aga att       629
Glu Asp Thr Ala Leu Arg Tyr Leu Asn Pro Gln Gln Tyr Tyr Arg Ile
        190                 195                 200 gtc aac ctc atg aag aag aaa cgt gca gaa cga gag ctt tat gtc gat       677
Val Asn Leu Met Lys Lys Lys Arg Ala Glu Arg Glu Leu Tyr Val Asp
    205                 210                 215 gag gtt gtc aat gaa gtg aag aaa cgt gtc gaa gaa gta aat atc aag       725
Glu Val Val Asn Glu Val Lys Lys Arg Val Glu Glu Val Asn Ile Lys
220                 225                 230                 235
```

```
-continued gct gac ttc tcg gga cgc ccg aaa cat att tac agc att tat cga aaa        773
Ala Asp Phe Ser Gly Arg Pro Lys His Ile Tyr Ser Ile Tyr Arg Lys
            240                 245                 250 atg gtg ctg caa aat aag caa ttc aat gaa att tac gat ttg ttg gct        821
Met Val Leu Gln Asn Lys Gln Phe Asn Glu Ile Tyr Asp Leu Leu Ala
            255                 260                 265 gtc cgt att ctt gtg aat agc ata aag gac tgc tac gcg gtg ctt ggc        869
Val Arg Ile Leu Val Asn Ser Ile Lys Asp Cys Tyr Ala Val Leu Gly
            270                 275                 280 atc att cac aca tgc tgg aaa ccg atg cca ggc aga ttc aaa gat tat        917
Ile Ile His Thr Cys Trp Lys Pro Met Pro Gly Arg Phe Lys Asp Tyr
        285                 290                 295 atc gca atg ccg aag ccg aat atg tat caa tcg ctt cat aca acg gtt        965
Ile Ala Met Pro Lys Pro Asn Met Tyr Gln Ser Leu His Thr Thr Val
300                 305                 310                 315 att ggg cct aaa gcg gat ccg ctt gaa gtg cag atc cgc acc ttt gaa       1013
Ile Gly Pro Lys Ala Asp Pro Leu Glu Val Gln Ile Arg Thr Phe Glu
                320                 325                 330 atg cat gaa ata gcg gaa tac ggg gtt gcg gct cac tgg gct tat aaa       1061
Met His Glu Ile Ala Glu Tyr Gly Val Ala Ala His Trp Ala Tyr Lys
            335                 340                 345 gaa ggg aaa gca gcc aat gaa ggt gca acc ttt gag aaa aag ctt tct       1109
Glu Gly Lys Ala Ala Asn Glu Gly Ala Thr Phe Glu Lys Lys Leu Ser
        350                 355                 360 tgg ttc cgt gaa att tta gaa ttt caa aat gaa tcg aca gat gca gaa       1157
Trp Phe Arg Glu Ile Leu Glu Phe Gln Asn Glu Ser Thr Asp Ala Glu
    365                 370                 375 gaa ttt atg gaa tcg ctc aaa att gat ttg ttc tct gac atg gtg tat       1205
Glu Phe Met Glu Ser Leu Lys Ile Asp Leu Phe Ser Asp Met Val Tyr
380                 385                 390                 395 gtc ttt acg cca aaa gga gat gta atc gag ctt ccg tcc ggt tct gtt       1253
Val Phe Thr Pro Lys Gly Asp Val Ile Glu Leu Pro Ser Gly Ser Val
                400                 405                 410 ccg att gac ttt tct tac cgg att cac tct gaa atc ggc aat aaa aca       1301
Pro Ile Asp Phe Ser Tyr Arg Ile His Ser Glu Ile Gly Asn Lys Thr
            415                 420                 425 atc ggt gcc aaa gta aac gga aaa atg gtt acg ctt gac cat aag ctt       1349
Ile Gly Ala Lys Val Asn Gly Lys Met Val Thr Leu Asp His Lys Leu
        430                 435                 440 cgg aca ggt gat atc gtt gaa att ctc acc tct aag cat tcc tac ggt       1397
Arg Thr Gly Asp Ile Val Glu Ile Leu Thr Ser Lys His Ser Tyr Gly
    445                 450                 455 ccg agc cag gat tgg gtg aag ctt gcc caa aca tcc caa gcg aag cat       1445
Pro Ser Gln Asp Trp Val Lys Leu Ala Gln Thr Ser Gln Ala Lys His
460                 465                 470                 475 aaa atc cgt caa ttc ttt aag aaa cag cgg cgt gaa gaa aat gtc gaa       1493
Lys Ile Arg Gln Phe Phe Lys Lys Gln Arg Arg Glu Glu Asn Val Glu
                480                 485                 490 aaa ggc cgt gag ctg gtc gaa aaa gaa att aaa aac ttg gat ttt gaa       1541
Lys Gly Arg Glu Leu Val Glu Lys Glu Ile Lys Asn Leu Asp Phe Glu
            495                 500                 505 ttg aag gat gtt tta acg ccg gag aat att caa aag gtt gct gac aaa       1589
Leu Lys Asp Val Leu Thr Pro Glu Asn Ile Gln Lys Val Ala Asp Lys
        510                 515                 520 ttt aat ttc tca aat gaa gag gat atg tac gcg gcg gtc ggt tac aac       1637
Phe Asn Phe Ser Asn Glu Glu Asp Met Tyr Ala Ala Val Gly Tyr Asn
    525                 530                 535 ggc atc aca gct ctg cag gtg gcg aac cgc cta aca gaa aaa gag aga       1685
Gly Ile Thr Ala Leu Gln Val Ala Asn Arg Leu Thr Glu Lys Glu Arg
```

```
540                 545                 550                 555
aag cag cgc gac cag gaa gaa cag gaa aag atc gtt cag gaa gtc act    1733
Lys Gln Arg Asp Gln Glu Glu Gln Glu Lys Ile Val Gln Glu Val Thr
                560                 565                 570 ggg gaa cct aag cca tac ccg caa gga aga aaa cgg gaa gct ggc gtt    1781
Gly Glu Pro Lys Pro Tyr Pro Gln Gly Arg Lys Arg Glu Ala Gly Val
            575                 580                 585 cgt gtc aag ggc att gac aac ctc ctt gtc cgt tta tca aaa tgc tgc    1829
Arg Val Lys Gly Ile Asp Asn Leu Leu Val Arg Leu Ser Lys Cys Cys
        590                 595                 600 aat cct gtg cca ggt gat gat att gtc ggc ttt atc aca aaa ggc aga    1877
Asn Pro Val Pro Gly Asp Asp Ile Val Gly Phe Ile Thr Lys Gly Arg
    605                 610                 615 ggg gtt tcg gtc cat cgc gaa gac tgt ccg aat gtc aaa acg aat gaa    1925
Gly Val Ser Val His Arg Glu Asp Cys Pro Asn Val Lys Thr Asn Glu
620                 625                 630                 635 gcc caa gag cgg ctg atc ccg gta gag tgg gaa cat gag tca caa gtt    1973
Ala Gln Glu Arg Leu Ile Pro Val Glu Trp Glu His Glu Ser Gln Val
                640                 645                 650 caa aag cgc aag gaa tac aat gtt gag ata gag att ctt ggg tat gac    2021
Gln Lys Arg Lys Glu Tyr Asn Val Glu Ile Glu Ile Leu Gly Tyr Asp
            655                 660                 665 cgc cgc gga ttg ctg aac gag gta ctc cag gca gtg aat gaa acg aaa    2069
Arg Arg Gly Leu Leu Asn Glu Val Leu Gln Ala Val Asn Glu Thr Lys
        670                 675                 680 acc aat att tca tct gtc tct ggc aaa tcg gat cgc aat aaa gtg gca    2117
Thr Asn Ile Ser Ser Val Ser Gly Lys Ser Asp Arg Asn Lys Val Ala
    685                 690                 695 acc atc cat atg gcg att ttt atc cag aat atc aat cac ttg cat aaa    2165
Thr Ile His Met Ala Ile Phe Ile Gln Asn Ile Asn His Leu His Lys
700                 705                 710                 715 gtc gtc gag cgt att aaa cag att aga gat atc tat tct gtg cgc cgc    2213
Val Val Glu Arg Ile Lys Gln Ile Arg Asp Ile Tyr Ser Val Arg Arg
                720                 725                 730 gtc atg aac taaaggggtt agaaaagaga ttagttgttc agcgagtaac            2262
Val Met Asn agaagcaagc gttaca                                                  2278

<210> SEQ ID NO 2
<211> LENGTH: 734
<212> TYPE: PRT
<213> ORGANISM: relA-bac

<400> SEQUENCE: 2

Met Ala Asn Glu Gln Val Leu Thr Ala Glu Gln Val Ile Asp Lys Ala
 1               5                  10                  15

Arg Ser Tyr Leu Ser Asp Glu His Ile Ala Phe Val Glu Lys Ala Tyr
                20                  25                  30

Leu Tyr Ala Glu Asp Ala His Arg Glu Gln Tyr Arg Lys Ser Gly Glu
            35                  40                  45

Pro Tyr Ile Ile His Pro Ile Gln Val Ala Gly Ile Leu Val Asp Leu
        50                  55                  60

Glu Met Asp Pro Ser Thr Ile Ala Gly Gly Phe Leu His Asp Val Val
65                  70                  75                  80

Glu Asp Thr Asp Val Thr Leu Asp Asp Leu Lys Glu Ala Phe Ser Glu
                85                  90                  95

Glu Val Ala Met Leu Val Asp Gly Val Thr Lys Leu Gly Lys Ile Lys
            100                 105                 110
```

-continued

```
Tyr Lys Ser Gln Glu Gln Gln Ala Glu Asn His Arg Lys Met Phe
        115                 120                 125
Val Ala Met Ala Gln Asp Ile Arg Val Ile Leu Ile Lys Leu Ala Asp
    130                 135                 140
Arg Leu His Asn Met Arg Thr Leu Lys His Leu Pro Gln Glu Lys Gln
145                 150                 155                 160
Arg Arg Ile Ser Asn Glu Thr Leu Glu Ile Phe Ala Pro Leu Ala His
                165                 170                 175
Arg Leu Gly Ile Ser Lys Ile Lys Trp Glu Leu Glu Asp Thr Ala Leu
            180                 185                 190
Arg Tyr Leu Asn Pro Gln Gln Tyr Tyr Arg Ile Val Asn Leu Met Lys
        195                 200                 205
Lys Lys Arg Ala Glu Arg Glu Leu Tyr Val Asp Glu Val Asn Glu
    210                 215                 220
Val Lys Lys Arg Val Glu Glu Val Asn Ile Lys Ala Asp Phe Ser Gly
225                 230                 235                 240
Arg Pro Lys His Ile Tyr Ser Ile Tyr Arg Lys Met Val Leu Gln Asn
                245                 250                 255
Lys Gln Phe Asn Glu Ile Tyr Asp Leu Leu Ala Val Arg Ile Leu Val
            260                 265                 270
Asn Ser Ile Lys Asp Cys Tyr Ala Val Leu Gly Ile Ile His Thr Cys
        275                 280                 285
Trp Lys Pro Met Pro Gly Arg Phe Lys Asp Tyr Ile Ala Met Pro Lys
    290                 295                 300
Pro Asn Met Tyr Gln Ser Leu His Thr Thr Val Ile Gly Pro Lys Ala
305                 310                 315                 320
Asp Pro Leu Glu Val Gln Ile Arg Thr Phe Glu Met His Glu Ile Ala
                325                 330                 335
Glu Tyr Gly Val Ala Ala His Trp Ala Tyr Lys Glu Gly Lys Ala Ala
            340                 345                 350
Asn Glu Gly Ala Thr Phe Glu Lys Lys Leu Ser Trp Phe Arg Glu Ile
        355                 360                 365
Leu Glu Phe Gln Asn Glu Ser Thr Asp Ala Glu Glu Phe Met Glu Ser
    370                 375                 380
Leu Lys Ile Asp Leu Phe Ser Asp Met Val Tyr Val Phe Thr Pro Lys
385                 390                 395                 400
Gly Asp Val Ile Glu Leu Pro Ser Gly Ser Val Pro Ile Asp Phe Ser
                405                 410                 415
Tyr Arg Ile His Ser Glu Ile Gly Asn Lys Thr Ile Gly Ala Lys Val
            420                 425                 430
Asn Gly Lys Met Val Thr Leu Asp His Lys Leu Arg Thr Gly Asp Ile
        435                 440                 445
Val Glu Ile Leu Thr Ser Lys His Ser Tyr Gly Pro Ser Gln Asp Trp
    450                 455                 460
Val Lys Leu Ala Gln Thr Ser Gln Ala Lys His Lys Ile Arg Gln Phe
465                 470                 475                 480
Phe Lys Lys Gln Arg Arg Glu Glu Asn Val Glu Lys Gly Arg Glu Leu
                485                 490                 495
Val Glu Lys Glu Ile Lys Asn Leu Asp Phe Glu Leu Lys Asp Val Leu
            500                 505                 510
Thr Pro Glu Asn Ile Gln Lys Val Ala Asp Lys Phe Asn Phe Ser Asn
        515                 520                 525
```

```
Glu Glu Asp Met Tyr Ala Ala Val Gly Tyr Asn Gly Ile Thr Ala Leu
    530                 535                 540

Gln Val Ala Asn Arg Leu Thr Glu Lys Glu Arg Lys Gln Arg Asp Gln
545                 550                 555                 560

Glu Glu Gln Glu Lys Ile Val Gln Val Thr Gly Glu Pro Lys Pro
                565                 570                 575

Tyr Pro Gln Gly Arg Lys Arg Glu Ala Gly Val Arg Val Lys Gly Ile
            580                 585                 590

Asp Asn Leu Leu Val Arg Leu Ser Lys Cys Cys Asn Pro Val Pro Gly
            595                 600                 605

Asp Asp Ile Val Gly Phe Ile Thr Lys Gly Arg Gly Val Ser Val His
            610                 615                 620

Arg Glu Asp Cys Pro Asn Val Lys Thr Asn Glu Ala Gln Glu Arg Leu
625                 630                 635                 640

Ile Pro Val Glu Trp Glu His Glu Ser Gln Val Gln Lys Arg Lys Glu
                645                 650                 655

Tyr Asn Val Glu Ile Glu Ile Leu Gly Tyr Asp Arg Arg Gly Leu Leu
                660                 665                 670

Asn Glu Val Leu Gln Ala Val Asn Glu Thr Lys Thr Asn Ile Ser Ser
            675                 680                 685

Val Ser Gly Lys Ser Asp Arg Asn Lys Val Ala Thr Ile His Met Ala
    690                 695                 700

Ile Phe Ile Gln Asn Ile Asn His Leu His Lys Val Val Glu Arg Ile
705                 710                 715                 720

Lys Gln Ile Arg Asp Ile Tyr Ser Val Arg Arg Val Met Asn
                725                 730

<210> SEQ ID NO 3
<211> LENGTH: 2239
<212> TYPE: DNA
<213> ORGANISM: relA-bac
<220> FEATURE:
<221> NAME/KEY: CDS
<222> LOCATION: (21)...(2225)

<400> SEQUENCE: 3
catttaaaaa aggtgattcc atg gcg aac gaa caa gta ttg act gcc gag caa      53
                     Met Ala Asn Glu Gln Val Leu Thr Ala Glu Gln
                       1               5                  10 gta ata gat aaa gcg cgc act tat ctg ccg gag gag cag att gcg ttt      101
Val Ile Asp Lys Ala Arg Thr Tyr Leu Pro Glu Glu Gln Ile Ala Phe
            15                  20                  25 gtt gag aaa gct tat ctg tat gcg caa gac gcg cat cgc gaa cag tat      149
Val Glu Lys Ala Tyr Leu Tyr Ala Gln Asp Ala His Arg Glu Gln Tyr
        30                  35                  40 cgc aaa tca ggt gag ccg tac atc att cat ccg att cag gtg gcg gga      197
Arg Lys Ser Gly Glu Pro Tyr Ile Ile His Pro Ile Gln Val Ala Gly
    45                  50                  55 atc ctc gtc gat ctg gaa atg gac cct tcc acg att gcg ggc gga ttt      245
Ile Leu Val Asp Leu Glu Met Asp Pro Ser Thr Ile Ala Gly Gly Phe
60                  65                  70                  75 ctg cat gac gtg gtc gag gac acg gat gtc acc ctc gat gac ctg aag      293
Leu His Asp Val Val Glu Asp Thr Asp Val Thr Leu Asp Asp Leu Lys
                80                  85                  90 gaa gca ttt tct gaa gaa gtg gcg atg ctt gtc gac ggt gta acg aag      341
Glu Ala Phe Ser Glu Glu Val Ala Met Leu Val Asp Gly Val Thr Lys
            95                 100                 105 ctc ggt aaa att aag tat aaa tct caa gag gag cag cag gcg gaa aac      389
```

-continued

| | | | | | | | | | | | | | | | |
|---|---|---|---|---|---|---|---|---|---|---|---|---|---|---|---|
| Leu | Gly | Lys | Ile | Lys | Tyr | Lys | Ser | Gln | Glu | Gln | Gln | Ala | Glu | Asn | |
| | | 110 | | | | | 115 | | | | 120 | | | | |

```
cat cga aaa atg ttt gtc gct atg gct cag gat atc aga gtc ata ttg      437
His Arg Lys Met Phe Val Ala Met Ala Gln Asp Ile Arg Val Ile Leu
    125             130                 135 atc aag ctg gcg gat cgc ctt cat aat atg cgg acg tta aag cat ctt      485
Ile Lys Leu Ala Asp Arg Leu His Asn Met Arg Thr Leu Lys His Leu
140             145                 150                 155 ccg cag gaa aag cag cgg aga att tca aat gag acg ctg gaa atc ttc      533
Pro Gln Glu Lys Gln Arg Arg Ile Ser Asn Glu Thr Leu Glu Ile Phe
                160                 165                 170 gct ccg ctg gcc cat cgg ctc ggg att tct aag atc aaa tgg gag ctt      581
Ala Pro Leu Ala His Arg Leu Gly Ile Ser Lys Ile Lys Trp Glu Leu
            175                 180                 185 gaa gac acc gct ctc cgt tat ttg aat cct cag caa tat tac aga atc      629
Glu Asp Thr Ala Leu Arg Tyr Leu Asn Pro Gln Gln Tyr Tyr Arg Ile
        190                 195                 200 gtt aac ctc atg aag aaa aag cgc gcg gaa cgc gaa ctt tat gtc gat      677
Val Asn Leu Met Lys Lys Lys Arg Ala Glu Arg Glu Leu Tyr Val Asp
    205                 210                 215 gag gtt gtc aat gaa gtg aaa aaa cgc gtc gaa gaa gtg aat atc aaa      725
Glu Val Val Asn Glu Val Lys Lys Arg Val Glu Glu Val Asn Ile Lys
220                 225                 230                 235 gcg gac ttt tca ggc cgt ccg aag cac atc tac agc att tac cgc aag      773
Ala Asp Phe Ser Gly Arg Pro Lys His Ile Tyr Ser Ile Tyr Arg Lys
                240                 245                 250 atg gcg ctg caa aat aaa cag ttt aat gaa ata tat gat ctg ctc gcc      821
Met Ala Leu Gln Asn Lys Gln Phe Asn Glu Ile Tyr Asp Leu Leu Ala
            255                 260                 265 gtc cgt att ctt gtc gga agc att aaa gac tgc tac gcc gta ctc ggc      869
Val Arg Ile Leu Val Gly Ser Ile Lys Asp Cys Tyr Ala Val Leu Gly
        270                 275                 280 att att cat acg tgc tgg aag ccg atg ccg ggc aga ttc aaa gat tat      917
Ile Ile His Thr Cys Trp Lys Pro Met Pro Gly Arg Phe Lys Asp Tyr
    285                 290                 295 att gcg atg cct aag ccg aat atg tat cag tcc ctg cat acg aca gta      965
Ile Ala Met Pro Lys Pro Asn Met Tyr Gln Ser Leu His Thr Thr Val
300                 305                 310                 315 atc ggg cct aaa ggc gat ccg ctg gaa gtg cag atc aga acg ttt gag     1013
Ile Gly Pro Lys Gly Asp Pro Leu Glu Val Gln Ile Arg Thr Phe Glu
                320                 325                 330 atg cat gag atc gct gaa tac ggg gtg gct gca cac tgg gca tat aaa     1061
Met His Glu Ile Ala Glu Tyr Gly Val Ala Ala His Trp Ala Tyr Lys
            335                 340                 345 gaa ggc aag gct gca aac gaa gaa gcg aca ttt gag aaa aaa ctg tcc     1109
Glu Gly Lys Ala Ala Asn Glu Glu Ala Thr Phe Glu Lys Lys Leu Ser
        350                 355                 360 tgg ttc cgc gaa att ctg gaa ttc caa aac gaa tct acc gat gcg gaa     1157
Trp Phe Arg Glu Ile Leu Glu Phe Gln Asn Glu Ser Thr Asp Ala Glu
    365                 370                 375 gaa ttt atg gaa tcg ctg aaa atc gat tta ttt tct gac atg gta tac     1205
Glu Phe Met Glu Ser Leu Lys Ile Asp Leu Phe Ser Asp Met Val Tyr
380                 385                 390                 395 gta ttt acg cca aaa ggc gat gtc att gaa ctg ccg tca ggc tct gta     1253
Val Phe Thr Pro Lys Gly Asp Val Ile Glu Leu Pro Ser Gly Ser Val
                400                 405                 410 ccg att gat ttt tcc tac agg att cac tcc gag atc ggc aac aaa acc     1301
Pro Ile Asp Phe Ser Tyr Arg Ile His Ser Glu Ile Gly Asn Lys Thr
            415                 420                 425
```

```
                                         -continued atc gga gcg aaa gtg aac ggg aaa atg gtg acg ctt gac cat aag ctc     1349
Ile Gly Ala Lys Val Asn Gly Lys Met Val Thr Leu Asp His Lys Leu
            430                 435                 440 cgg acg ggc gac att gtc gaa atc gtg acg tcc aag cat tca tac gat     1397
Arg Thr Gly Asp Ile Val Glu Ile Val Thr Ser Lys His Ser Tyr Asp
445                 450                 455 ccg agt caa gac tgg atc aaa ctc gca cag acg tca cag gcg aaa cac     1445
Pro Ser Gln Asp Trp Ile Lys Leu Ala Gln Thr Ser Gln Ala Lys His
460                 465                 470                 475 aaa atc cgc caa ttc ttc aag aaa cag cgc cgt gaa gaa aat gtc gaa     1493
Lys Ile Arg Gln Phe Phe Lys Lys Gln Arg Arg Glu Glu Asn Val Glu
                480                 485                 490 aaa ggc cgt gag ctg gtc gaa aaa gaa att aaa aat ctt gat ttt gaa     1541
Lys Gly Arg Glu Leu Val Glu Lys Glu Ile Lys Asn Leu Asp Phe Glu
            495                 500                 505 gtg aag gaa gtt tta acg ctc gaa aac ctt caa aag gtt gcc gac aag     1589
Val Lys Glu Val Leu Thr Leu Glu Asn Leu Gln Lys Val Ala Asp Lys
            510                 515                 520 ttc aat ttc tca aat gaa gag gat atg tac gcg gcg gtc ggg tat aac     1637
Phe Asn Phe Ser Asn Glu Glu Asp Met Tyr Ala Ala Val Gly Tyr Asn
525                 530                 535 ggg att acc gct ttg cag gtg gca aac agg ctc acc gaa aaa gaa cgg     1685
Gly Ile Thr Ala Leu Gln Val Ala Asn Arg Leu Thr Glu Lys Glu Arg
540                 545                 550                 555 aag ctg cgt gat cag gaa gag cag gaa aaa atc gtt cag gaa gtc act     1733
Lys Leu Arg Asp Gln Glu Glu Gln Glu Lys Ile Val Gln Glu Val Thr
                560                 565                 570 tcc gag ccg aaa cag tat ccg caa ggg aga aaa cgg gaa gcg ggt gtg     1781
Ser Glu Pro Lys Gln Tyr Pro Gln Gly Arg Lys Arg Glu Ala Gly Val
            575                 580                 585 cgc gtg aaa ggc atc gac aac ctt ctc gtc cgt ctg tcg aaa tgc tgc     1829
Arg Val Lys Gly Ile Asp Asn Leu Leu Val Arg Leu Ser Lys Cys Cys
            590                 595                 600 aac ccg gtg cca ggc gat cat att gtc ggt ttt att aca aaa ggg cgc     1877
Asn Pro Val Pro Gly Asp His Ile Val Gly Phe Ile Thr Lys Gly Arg
605                 610                 615 ggt gta tcc gtt cac cgt gat gac tgt ccg aac gta aaa acg aat gaa     1925
Gly Val Ser Val His Arg Asp Asp Cys Pro Asn Val Lys Thr Asn Glu
620                 625                 630                 635 gcg cag gaa cga ttg atc cct gtt gaa tgg gag cat gaa tca caa gtt     1973
Ala Gln Glu Arg Leu Ile Pro Val Glu Trp Glu His Glu Ser Gln Val
                640                 645                 650 caa aga cgc aaa gaa tat aac gtt gag att gag att ctg ggg tat gac     2021
Gln Arg Arg Lys Glu Tyr Asn Val Glu Ile Glu Ile Leu Gly Tyr Asp
            655                 660                 665 cgt ctc ggg ctg tta aat gaa gtg ctt cag gcc gta aac gaa acg aaa     2069
Arg Leu Gly Leu Leu Asn Glu Val Leu Gln Ala Val Asn Glu Thr Lys
            670                 675                 680 acc aac atc tcg tct gtc tcg ggc aaa tcc gac cgc aat aaa gtc gct     2117
Thr Asn Ile Ser Ser Val Ser Gly Lys Ser Asp Arg Asn Lys Val Ala
685                 690                 695 acg att cat atg gcg att ttt att caa aac atc aat cat ctg cac aaa     2165
Thr Ile His Met Ala Ile Phe Ile Gln Asn Ile Asn His Leu His Lys
700                 705                 710                 715 gtg gtc gag cgg att aag cag atc aga gac ata tat tca gtc cgc cgg     2213
Val Val Glu Arg Ile Lys Gln Ile Arg Asp Ile Tyr Ser Val Arg Arg
                720                 725                 730 gta atg aac taa aaggagcttg ctat                                     2239
Val Met Asn
```

-continued

```
<210> SEQ ID NO 4
<211> LENGTH: 734
<212> TYPE: PRT
<213> ORGANISM: relA-bac

<400> SEQUENCE: 4

Met Ala Asn Glu Gln Val Leu Thr Ala Glu Gln Val Ile Asp Lys Ala
 1               5                  10                  15

Arg Thr Tyr Leu Pro Glu Gln Ile Ala Phe Val Glu Lys Ala Tyr
            20                  25                  30

Leu Tyr Ala Gln Asp Ala His Arg Glu Gln Tyr Arg Lys Ser Gly Glu
            35                  40                  45

Pro Tyr Ile Ile His Pro Ile Gln Val Ala Gly Ile Leu Val Asp Leu
    50                  55                  60

Glu Met Asp Pro Ser Thr Ile Ala Gly Gly Phe Leu His Asp Val Val
65                  70                  75                  80

Glu Asp Thr Asp Val Thr Leu Asp Asp Leu Lys Glu Ala Phe Ser Glu
                85                  90                  95

Glu Val Ala Met Leu Val Asp Gly Val Thr Lys Leu Gly Lys Ile Lys
            100                 105                 110

Tyr Lys Ser Gln Glu Glu Gln Gln Ala Glu Asn His Arg Lys Met Phe
        115                 120                 125

Val Ala Met Ala Gln Asp Ile Arg Val Ile Leu Ile Lys Leu Ala Asp
130                 135                 140

Arg Leu His Asn Met Arg Thr Leu Lys His Leu Pro Gln Glu Lys Gln
145                 150                 155                 160

Arg Arg Ile Ser Asn Glu Thr Leu Glu Ile Phe Ala Pro Leu Ala His
                165                 170                 175

Arg Leu Gly Ile Ser Lys Ile Lys Trp Glu Leu Glu Asp Thr Ala Leu
            180                 185                 190

Arg Tyr Leu Asn Pro Gln Gln Tyr Tyr Arg Ile Val Asn Leu Met Lys
        195                 200                 205

Lys Lys Arg Ala Glu Arg Glu Leu Tyr Val Asp Glu Val Val Asn Glu
    210                 215                 220

Val Lys Lys Arg Val Glu Glu Val Asn Ile Lys Ala Asp Phe Ser Gly
225                 230                 235                 240

Arg Pro Lys His Ile Tyr Ser Ile Tyr Arg Lys Met Ala Leu Gln Asn
                245                 250                 255

Lys Gln Phe Asn Glu Ile Tyr Asp Leu Leu Ala Val Arg Ile Leu Val
            260                 265                 270

Gly Ser Ile Lys Asp Cys Tyr Ala Val Leu Gly Ile Ile His Thr Cys
        275                 280                 285

Trp Lys Pro Met Pro Gly Arg Phe Lys Asp Tyr Ile Ala Met Pro Lys
    290                 295                 300

Pro Asn Met Tyr Gln Ser Leu His Thr Thr Val Ile Gly Pro Lys Gly
305                 310                 315                 320

Asp Pro Leu Glu Val Gln Ile Arg Thr Phe Glu Met His Glu Ile Ala
                325                 330                 335

Glu Tyr Gly Val Ala Ala His Trp Ala Tyr Lys Glu Gly Lys Ala Ala
            340                 345                 350

Asn Glu Glu Ala Thr Phe Glu Lys Lys Leu Ser Trp Phe Arg Glu Ile
        355                 360                 365

Leu Glu Phe Gln Asn Glu Ser Thr Asp Ala Glu Glu Phe Met Glu Ser
    370                 375                 380
```

-continued

Leu Lys Ile Asp Leu Phe Ser Asp Met Val Tyr Val Phe Thr Pro Lys
385                 390                 395                 400

Gly Asp Val Ile Glu Leu Pro Ser Gly Ser Val Pro Ile Asp Phe Ser
            405                 410                 415

Tyr Arg Ile His Ser Glu Ile Gly Asn Lys Thr Ile Gly Ala Lys Val
            420                 425                 430

Asn Gly Lys Met Val Thr Leu Asp His Lys Leu Arg Thr Gly Asp Ile
            435                 440                 445

Val Glu Ile Val Thr Ser Lys His Ser Tyr Asp Pro Ser Gln Asp Trp
    450                 455                 460

Ile Lys Leu Ala Gln Thr Ser Gln Ala Lys His Lys Ile Arg Gln Phe
465                 470                 475                 480

Phe Lys Lys Gln Arg Arg Glu Glu Asn Val Glu Lys Gly Arg Glu Leu
            485                 490                 495

Val Glu Lys Glu Ile Lys Asn Leu Asp Phe Glu Val Lys Glu Val Leu
            500                 505                 510

Thr Leu Glu Asn Leu Gln Lys Val Ala Asp Lys Phe Asn Phe Ser Asn
    515                 520                 525

Glu Glu Asp Met Tyr Ala Ala Val Gly Tyr Asn Gly Ile Thr Ala Leu
    530                 535                 540

Gln Val Ala Asn Arg Leu Thr Glu Lys Glu Arg Lys Leu Arg Asp Gln
545                 550                 555                 560

Glu Glu Gln Glu Lys Ile Val Gln Glu Val Thr Ser Glu Pro Lys Gln
            565                 570                 575

Tyr Pro Gln Gly Arg Lys Arg Glu Ala Gly Val Arg Val Lys Gly Ile
            580                 585                 590

Asp Asn Leu Leu Val Arg Leu Ser Lys Cys Cys Asn Pro Val Pro Gly
    595                 600                 605

Asp His Ile Val Gly Phe Ile Thr Lys Gly Arg Gly Val Ser Val His
    610                 615                 620

Arg Asp Asp Cys Pro Asn Val Lys Thr Asn Glu Ala Gln Glu Arg Leu
625                 630                 635                 640

Ile Pro Val Glu Trp Glu His Glu Ser Gln Val Gln Arg Arg Lys Glu
            645                 650                 655

Tyr Asn Val Glu Ile Glu Ile Leu Gly Tyr Asp Arg Leu Gly Leu Leu
            660                 665                 670

Asn Glu Val Leu Gln Ala Val Asn Glu Thr Lys Thr Asn Ile Ser Ser
    675                 680                 685

Val Ser Gly Lys Ser Asp Arg Asn Lys Val Ala Thr Ile His Met Ala
    690                 695                 700

Ile Phe Ile Gln Asn Ile Asn His Leu His Lys Val Val Glu Arg Ile
705                 710                 715                 720

Lys Gln Ile Arg Asp Ile Tyr Ser Val Arg Arg Val Met Asn
            725                 730

<210> SEQ ID NO 5
<211> LENGTH: 30
<212> TYPE: DNA
<213> ORGANISM: Primer

<400> SEQUENCE: 5
ccgaattcaa aggtgattcc atggcgaacg                             30

<210> SEQ ID NO 6

```
<211> LENGTH: 27
<212> TYPE: DNA
<213> ORGANISM: Primer

<400> SEQUENCE: 6
ccgaattcgg tgattccatg gcgaacg                                              27

<210> SEQ ID NO 7
<211> LENGTH: 19
<212> TYPE: DNA
<213> ORGANISM: Primer

<400> SEQUENCE: 7
gcggatccgc tttaggccc                                                       19

<210> SEQ ID NO 8
<211> LENGTH: 20
<212> TYPE: DNA
<213> ORGANISM: Primer

<400> SEQUENCE: 8
catgcatttc aaaggtgcgg                                                      20

<210> SEQ ID NO 9
<211> LENGTH: 22
<212> TYPE: DNA
<213> ORGANISM: Primer

<400> SEQUENCE: 9
cctttagttc atgacgcggc gc                                                   22

<210> SEQ ID NO 10
<211> LENGTH: 30
<212> TYPE: DNA
<213> ORGANISM: DNA

<400> SEQUENCE: 10
gtgtttagcg gccgctgaac aactaatctc                                           30

<210> SEQ ID NO 11
<211> LENGTH: 27
<212> TYPE: DNA
<213> ORGANISM: Primer

<400> SEQUENCE: 11
ataagcatgc gctgaacaac taatctc                                              27
```